US00PP10986P

United States Patent [19]

Roberson

[11] Patent Number: Plant 10,986

[45] Date of Patent: Jun. 29, 1999

[54] *CANNA GENERALIS* PLANT NAMED 'ROBLIBWAT'

[76] Inventor: Robert J. Roberson, 31706 E. Pink Hill Rd., Grain Valley, Jackson County, Mo. 64029

[21] Appl. No.: 08/985,078

[22] Filed: Dec. 4, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Ashwin Mehta
*Attorney, Agent, or Firm*—Rothwell, Figg, Ernst & Kurz

[57] ABSTRACT

A new and distinct cultivar of *Canna generalis* plant, substantially as described and illustrated herein, characterized particularly as to novelty by its intense watermelon -pink bloom coloring, dependable semi-dwarf growth habit, tendency to shed bloom florets quickly, hardy, robust rhizomes, slow tendency to set seed, resistance to leaf roller worms, and reddish burgundy edged green foliage which has extremely sustained health and beauty throughout the season providing a cultivar well suited as a garden or pot plant having no unusual susceptibility to the traditional Canna diseases and insects.

2 Drawing Sheets

SUMMARY OF THE INVENTION

This invention relates to a new and distinct Canna cultivar which is outstanding because of its intense watermelon-pink bloom coloring, its dependable semi-dwarf growth habit, its tendency to shed bloom florets quickly, its hardy, robust rhizomes, its slow tendency to set seed, its resistance to leaf roller worms, and its reddish burgundy edged green foliage which has extremely sustained health and beauty throughout the season. This selection was made from a specially designed Canna hybridizing program with said hybrid cultivars being planted and grown in Grain Valley, Mo.

ORIGIN AND ASEXUAL REPRODUCTION

Asexual reproduction of this cultivar by dividing the rhizome was directed by me, such reproduction establishing that the plant does in fact maintain the characteristics described, in successive generations.

It should be noted that the plant was initially selected from a Canna planting being grown near Grain Valley, Mo. in a cultivated area and has since been reproduced by dividing the rhizome in the vicinity of Grain Valley, Mo. with the new and distinct characteristics stated herein, found to be maintained through successive generations as before recited.

*Canna generalis* is a group of tropical to sub-tropical herbaceous plants grown primarily for their rapid growth and vivid, flamboyant, summer blooms. They are grown in USDA zones 9–10 as a perennial and in USDA zones 3–8 as an annual. General growth habit includes an erect central (main) stalk with large tropical alternate leaves. This massive plant, usually 24"–96" in height, is topped by a colorful, inflorescent display. They are of easy cultivation in any fertile, moist soil, especially soils high in humus.

The cultivar of *Canna generalis* 'Roblibwat' may further be described as having a number of distinctive characteristics which are enumerated in the succeeding specific description but broadly stated as comprising intense watermelon-pink bloom coloring, dependable semi-dwarf growth habit, tendency to shed bloom florets quickly, hardy, robust rhizomes, slow tendency to set seed, resistance to leaf roller worms, and reddish burgundy edged green foliage which has extremely sustained health and beauty throughout the season. The floral display has flowers of bright pink of (PMS#212). The bloom period begins at approximately 12 weeks after planting and continues until frost.

I have chosen to identify this new cultivar as *Canna generalis* 'Roblibwat'. This cultivar is being marketed in the United States under the name of Liberty (tm) Watermelon.

BRIEF DESCRIPTION OF THE DRAWING

The accompanying photographs shows as nearly true as it is reasonably possible to make the same, in a color illustration of this character, typical flowers and leaves of the new variety. The photographic drawings illustrates the flower form, the novel and distinctive pink flowers color, and the forest green foliage.

In the photograph.

DETAILED DESCRIPTION

Figure 1:
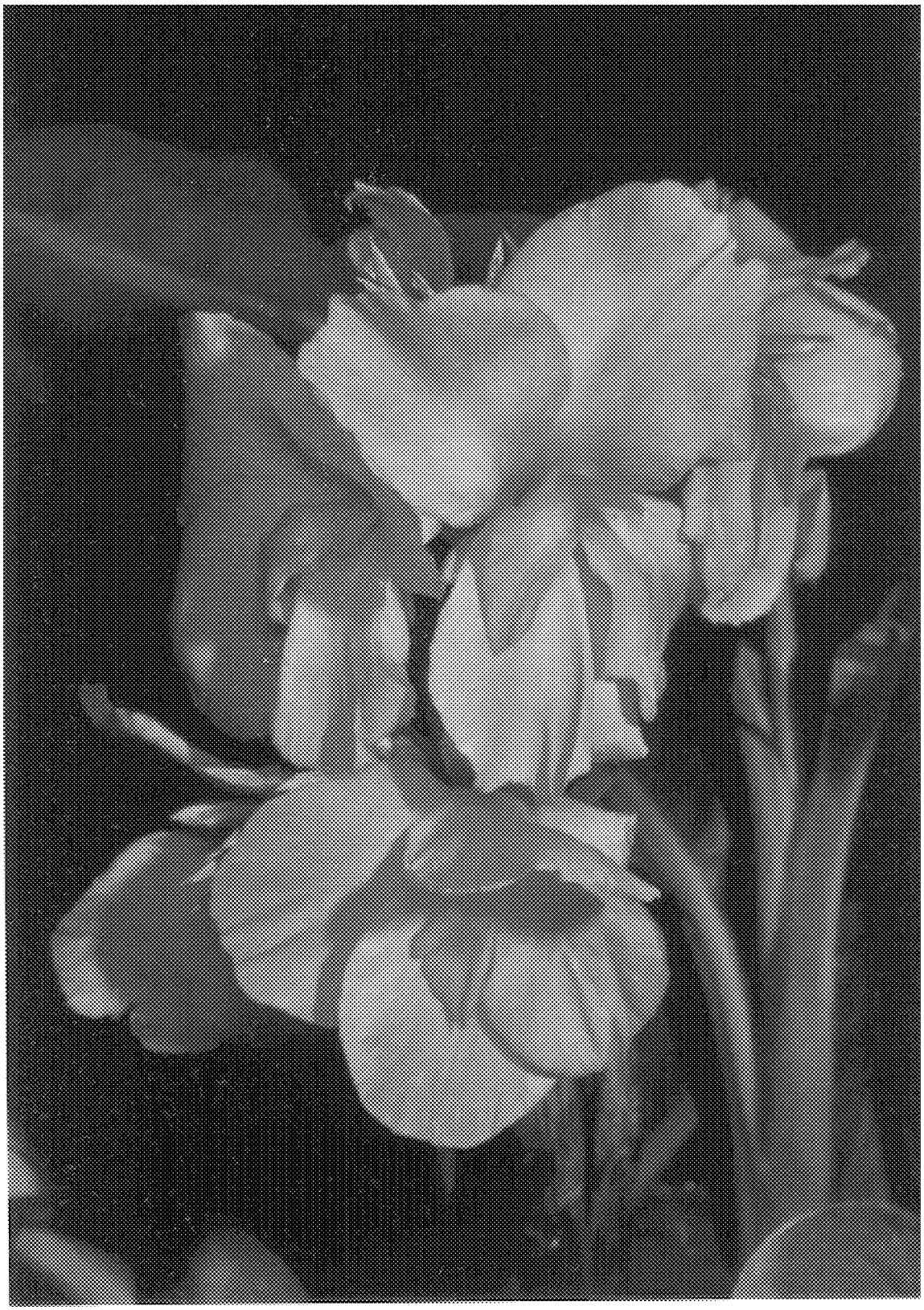
FIG. 1 illustrates the mature flower.
Figure 2:
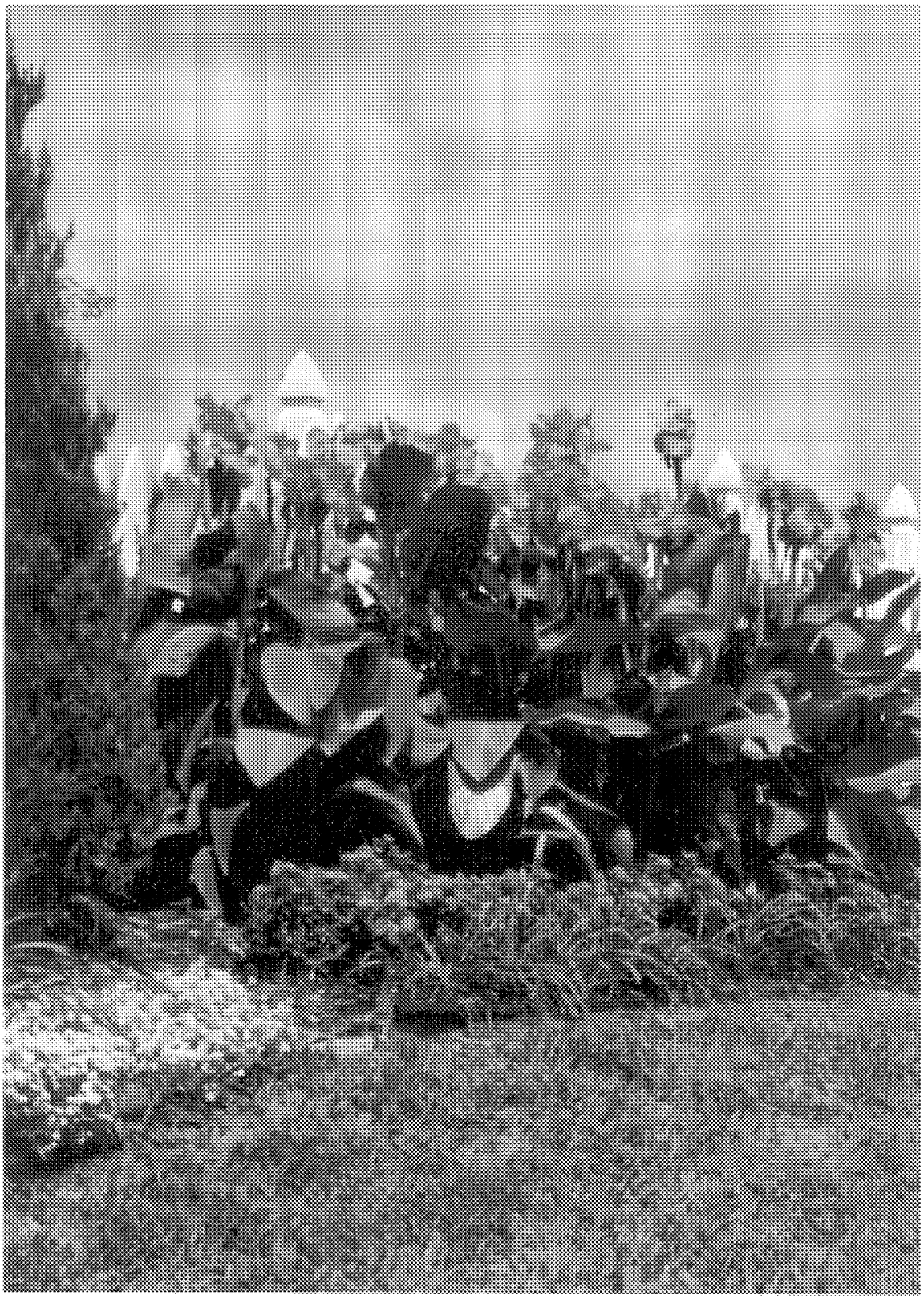
FIG. 2 illustrates the mature plant in mass.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo., unless stated otherwise.

Parentage:

*Seed parent.*—*Canna generalis* hybrid "North Star Red" (not patented).

*Pollen parent.*—Unknown; open pollinated.

Propagation: Asexual reproduction by rhizome division started near Grain Valley, Mo.

Plant descriptions:

*Inflorescence and reproductive parts.*—The overall inflorescence is thrysoid (mixed) and is approximately 28 cm in length by 19 cm in width when mature. The terminal axis is indeterminate and the lateral axis are cymose and determinate. The large, zygomorphic, hermaphrodite flowers are borne terminally and more or less erect in a racemose inflorescence and are at anthesis together with one that is in bud. The flowers, borne on short pedicels occur in pairs forming a two-flowered cincinnus. Each flower is subtended by a bract. The outer whorl of the perianth consists of three free, imbricate sepals, the inner whorl of three basically united petals. There are typically three to five petaloid staminodes (showy portion of inflorescence) with the smaller fertile petaloid stamen and style visible at the center of the flower. Colors of "Petals" (showy portion composed of petaloid staminodes): PMS #212 bright pink. The perianth segments (petals and sepals) are also PMS #212. Due to the unusual composition of the reproductive parts, self pollination is more common in cannas than is cross pollination. The petaloid stamen and style are visible at the center of the flower. The stamen can be recognized by the presence of the single anther-cell along its upper margin. The pistil is made up of the stigma or tip, the petaloid style and a three locular ovary. The ovary is borne on a short pedicel and each loculus contains numerous anatropous ovules attached to an axile placenta. The rarely formed capsule has a warty pericarp that disintegrates at maturity to release the seeds.

*Fragrance.*—None detected.

*Terminal axis.*—Indeterminate.

*Lateral axis.*—Cymose and determinate.

*Petaloid staminodes.*—Pink (PMS #212) (bright pink).

*Perianth segments.*—PMS #Pink (212).

*Bud at approximately one week prior to opening.*—5.5 cm to 7.6 cm which is comprised of: Sepal — 0.9 cm to 1.4 cm; Petal — 0.9 cm to 1.4 cm; and Emerging stamenodes—Varying from 1.6 cm to 4.3 cm.

Color of reproductive parts:

*Anther.*—brown(PMS#438) to black at dehiscence.

*Stigma.*—Translucent cream.

*Ovary.*—medium green (PMS#369).

*Stamen.*—Pink blend, similar to inflorescence.

*Style.*—Pink blend similar to inflorescence.

*Seeds.*—At maturity are near black, and approximately 4 mm by 7mm in size.

Leaves: The alternate leaves are long ovate in shape and have pinnate veins and a dominate mid-rib. They are large, brad, simple, and entire with sheathing petioles. The average size of leaves at maturity is 53 cm in length by 28 cm in width. The dominate color in young leaves is light green (PMS #365) with burgundy (PMS#483) on both front and back edges and dark green (PMS #349) on both front and back at maturity.

Tubers (rhizomes): These tuberous rhizomes are cream & burgundy in color when immature, and transitions into a red-burgundy (PMS #484) at maturity. The rhizomes are covered by a papery scale like leaves. This paper layering is brown (PMS #439) with darker brown (PMS #440) veining. The average rhizome is 11 cm in length and 2.8 cm in width.

Roots: The fleshy roots arise from the internodes of the rhizomes and vary from 1.1 to 3.2 mm in diameter and are an average length of 32.1 cm.

Flowering time: The bloom period begins at approximately 12 weeks after planting (when planted at the recommended season and given reasonable care) and continues until frost. No pruning or pinching is required for optimum flowering performance. Spent blooms are shed quickly (approximately 30 hours after opening).

Diseases: No known unusual susceptibility to diseases noted to date.

Insects: No known unusual susceptibility to insects noted to date.

General Observations

*Canna generalis* 'Roblibwat' with it's intense watermelon-pink bloom coloring, dependable semi-dwarf growth habit, tendency to shed bloom florets quickly, hardy, robust rhizomes, slow tendency to set seed, resistance to leaf roller worms, and reddish burgundy edged green foliage which has extremely sustained health and beauty throughout the season is striking in the landscape.

For the purpose of ornamental horticulture in our present living environments which include smaller yards and patio gardening, 'Roblibwat' is ideal due to several characteristics. These plant characteristics are:

A. Colors of Inflorescence and leaves: The carrying power (visibility) of this cultivar's pink inflorescence contrast the rich green foliage for a striking landscape display.

B. Dwarf Stature: The hybridizer achieved the dwarf height (3 feet) of this canna hybrid by serial selection of new cultivars from his breeding program.

C. Compact Growth: Another goal was to achieve compact growth habit in a cultivar displaying the striking bright pink bloom. The achievement of this growth habit is primarily shown by two characteristics: The stem thickness to height ratio and the internode spacing.

For example: In Cannas 'Roblibwat', the stem thickness (1½") to average height (36") ratio is 1 to 24. In the comparison plant, "Pink President", the stem thickness (1½") to height (54") is 1 to 36. The internode spacing of "Pink President" is 8½" and the internode spacing of 'Roblibwat' is 6¾" which creates a more dense, compact presentation.

This dwarf and compact growth habit makes 'Roblibwat' ideal for today's small garden and landscape designs and the patio/pot culture trend.

D. High Multiplication Rate: For commercial production, plant increase (multiplication rate) is very important. 'Roblibwat' increases an average of 11 rhizomes in USDA zone 5 in one season (5 month period) and as high as 14 rhizomes in a USDA zone 9 within one year. This is ideal for production and marketing. Though there are a few cannas of either dwarf stature or adequate multiplication rate, or bright pink inflorescence against green leaves in today's market, applicant is not aware of any that meet all these criteria as completely as does 'Roblibwat'.

E. Winter Storage: The storage capability of 'Roblibwat' is another characteristic that renders this cultivar advantageous both to home gardeners and to commercial growers. The rhizomes are superior for storage because an average of 95% of stored rhizomes are viable after the winter storage period.

The winter storage capability of 'Roblibwat' is very important for two reasons. Since cannas are only grown as perennials in USDA zones 9–10 and must be dug and stored in zones 3–8, a vast majority of home gardeners must routinely dig and store the rhizomes during the winter months. There is great variance as to the ability of different varieties to store successfully. 'Roblibwat' survives winter storage with a high rate of success. Secondly, this storage ability of 'Roblibwat' is of great advantage to commercial canna growers in USDA zones where the cannas must be dug and stored over winter months and a high degree of plant loss renders the product of no marketable value.

Comparison to Known Varieties

The cultivar may be compared with known varieties along the following lines.

*Canna generalis* 'Pink President' is an appropriate choice for a comparison to *Canna generalis* 'Roblibwat' because of the color combination of it's green foliage and coral pink bloom. Though 'Pink President' has coral-pink blooms and green foliage, there are three distinguishing characteristics which have been improved upon in 'Roblibwat'. These are (1) the pink color of 'Roblibwat' has less coral or orange and would be considered by the observer as a more "true" pink. 'Roblibwat' bloom PMS #212 to 'Pink President' PMS #184. (2) 'Roblibwat' is improved for today's demand for dwarf cannas as it is shorter than 'Pink President', i.e., 'Roblibwat' is 3 feet compared to 'Pink President's' height is 4½feet. (3) 'Roblibwat' maintains a "cleaner" overall presentation in the landscape than 'Pink President'. This is due to (a) its inforescence shedding blooms before they are noticeably spent; and (b) the foliage remains fresher, cleaner, and more vigorous for a longer period of the season than that of 'Pink President', i.e., 'Roblibwat' 4 months as compared to 'Pink President' 3 months.

*Canna generalis* 'North Star Red' is the seed parent of 'Roblibwat'. The most significant difference between these two cultivars is their color. 'North Star Red' is a red color as compared to the instant variety's color of pink.

I claim:

1. A new and distinct cultivar of *Canna generalis* plant, substantially as described and illustrated herein, characterized particularly as to novelty by its intense watermelon-pink bloom coloring, dependable semi-dwarf growth habit, tendency to shed bloom florets quickly, hardy, robust rhizomes, slow tendency to set seed, resistance to leaf roller worms, and reddish burgundy edged green foliage which has extremely sustained health and beauty throughout the season providing a cultivar well suited as a garden or pot plant having no unusual susceptibility to the traditional Canna diseases and insects.

* * * * *